United States Patent [19]

Krahn

[11] Plant 4,051

[45] May 10, 1977

[54] PEACH TREE

[75] Inventor: Henry Krahn, Sardis, Canada

[73] Assignee: May Nursery Company, Yakima, Wash.

[21] Appl. No.: 649,730

[22] Filed: Jan. 16, 1976

[51] Int. Cl.[2] ..... A01H 5/03
[52] U.S. Cl. ..... Plt./43
[58] Field of Search ..... Plt./43

*Primary Examiner*—Robert E. Bagwill
*Attorney, Agent, or Firm*—Christensen, O'Connor, Garrison & Havelka

[57] ABSTRACT

As a mutation of Pacific Gold, a new peach tree variety is disclosed which is characterized by its dwarf nature and a predominance of vigorous, robust spurs, very short laterals with short internodes and prominent axillary buds.

3 Drawing Figures

1

DESCRIPTION

This invention relates to a new and distinct variety of dwarf peach tree originating as a whole tree sport found growing among trees of the variety which has been sold in commerce under the name Pacific Gold (unpatented), the discovery having been made in the nursery of Fraser Valley Nursuries, Ltd., near Sardis, British Columbia, Canada.

The new variety has dwarf growth characteristics which make it possible to plant at closer spacings than the parent variety, Pacific Gold.

The tree and its progeny are characterized in part by a predominance of vigorous, robust spurs, very short laterals with short internodes and prominant axillary buds. The foliage is deep green and dense, the leaves are thinner and denser than the leaves of Pacific Gold with the early growth being very vigorous. The fruit of the new variety appears to be similar to that of Pacific Gold.

The discoverer has caused asexual reproduction of the new variety by means of budding in the abovesaid nursery, and has found the outstanding characteristics of the new variety to be permanent and stable.

FIG. 1 is a photograph of the new variety showing height and spread after 9 years of growth.

FIG. 2 is a photograph of trees of the new variety of 1 year with trees of the normal peach variety, Early Elberta, also 1 year of age appearing in the background.

FIG. 3 is a photograph of ripe fruit produced by the new variety.

2

TREE

Very small, full dwarf, vigorous growth and compact form; height—approximately 3 feet; spread—approximately 3 feet. It exhibits a predominance of vigorous, robust spurs, short laterals with short internodes and a predominance of axillary buds with limb and tree growth being approximately one-quarter of its parent and other standard size peach varieties.

FLOWERS AND LEAVES

The flowers of the new variety are double pink, very heavily clustered on the limbs due to the robust spurs, short laterals and short internodes. The leaves are dark green, longer and denser with approximately 25 percent more chlorophyll than those of its parent and other standard peach trees.

FRUIT

The fruit, similar to Pacific Gold, is generally large and attractive with a deep overall red blush. Flesh is juicy, flavor is very sweet. It is semi-freestone and ripens at substantially the same time as Pacific Gold (unpatented), approximately 7 to 10 days after the variety Redhaven.

I claim:

1. A new and distinct variety of peach tree characterized as to novelty primarily by the dwarf nature of its growth which is approximately one-quarter that of its parent Pacific Gold, foliage which is darker green, longer and denser with approximately 25 percent more chlorophyll than that of its parent Pacific Gold and with fruit similar to that of Pacific Gold and that ripens at substantially the same time as that of Pacific Gold.

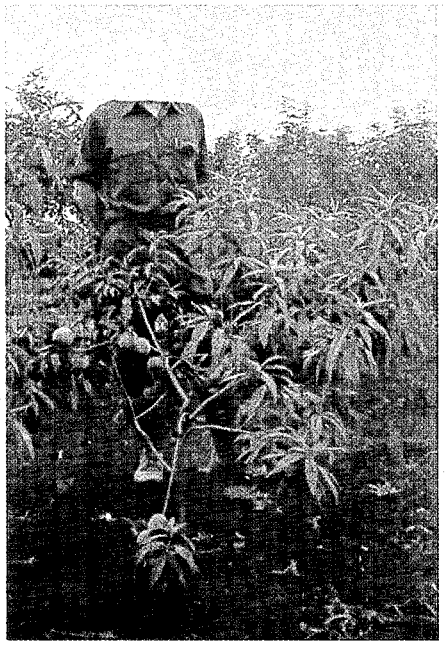
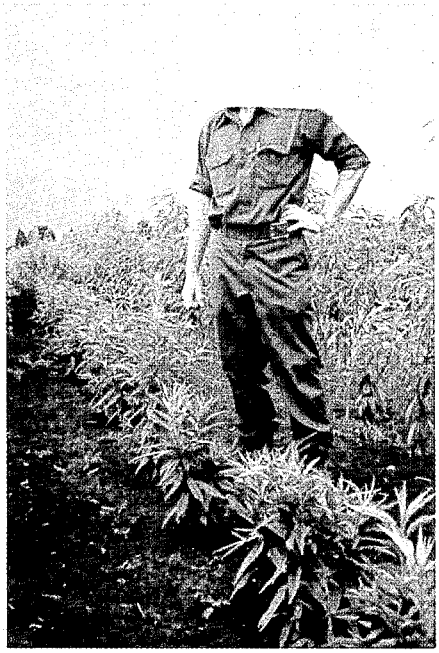
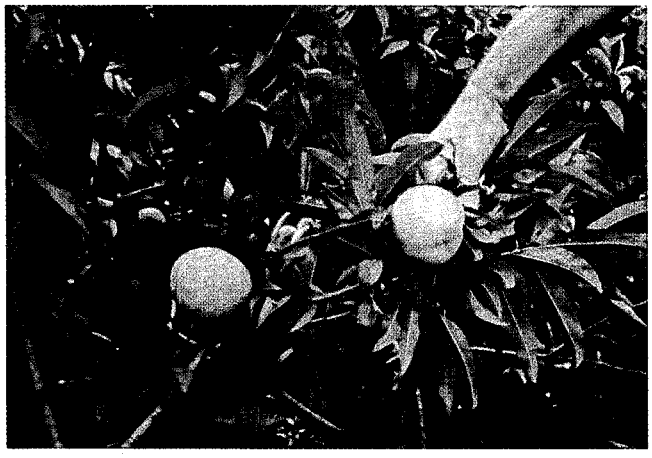

* * * * *